(12) United States Patent
Cheng et al.

(10) Patent No.: US 9,090,623 B2
(45) Date of Patent: Jul. 28, 2015

(54) COMPOUND JK12A AND PREPARATION THEREOF

(71) Applicant: LIANYUNGANG JINKANG HEXIN PHARMACEUTICAL CO., LTD., Lianyungang, Jiangsu (CN)

(72) Inventors: Yongzhi Cheng, Lianyungang (CN); Zhi Cheng, Lianyungang (CN); Min Zhou, Lianyungang (CN); Zhaojun Wang, Lianyungang (CN); Huizhen Li, Lianyungang (CN); Shenggang Fan, Lianyungang (CN)

(73) Assignee: Lianyungang Jinkang Hexin Pharmaceutical Co., Ltd., Jiangsu (CN)

( * ) Notice: Subject to any disclaimer, the term of this patent is extended or adjusted under 35 U.S.C. 154(b) by 0 days.

(21) Appl. No.: 14/394,434

(22) PCT Filed: Apr. 9, 2013

(86) PCT No.: PCT/CN2013/073959
§ 371 (c)(1),
(2) Date: Oct. 14, 2014

(87) PCT Pub. No.: WO2013/163917
PCT Pub. Date: Nov. 7, 2013

(65) Prior Publication Data
US 2015/0065708 A1 Mar. 5, 2015

(30) Foreign Application Priority Data

Apr. 13, 2012 (CN) .......................... 2012 1 0109743

(51) Int. Cl.
*C07D 487/18* (2006.01)
*C07D 475/04* (2006.01)
(52) U.S. Cl.
CPC ............ *C07D 487/18* (2013.01); *C07D 475/04* (2013.01)
(58) Field of Classification Search
CPC .................................................... C07D 487/18
USPC .......................................... 544/251; 514/250
See application file for complete search history.

(56) References Cited

U.S. PATENT DOCUMENTS 5,457,202 A   10/1995   Scheib et al.
6,441,168 B1   8/2002   Muller et al.

FOREIGN PATENT DOCUMENTS

| CN | 1063285 A | 8/1992 |
|----|-----------|--------|
| CN | 1122337 A | 5/1996 |
| CN | 1277197 A | 12/2000 |
| CN | 101143863 A | 3/2008 |
| CN | 101781637 A | 7/2010 |
| GR | 3029552 T3 | 6/1999 |

OTHER PUBLICATIONS

Kuroda et al., "Aplaminal: A Novel Cytotoxic Aminal Isolated from the Sea Hare Aplysia Kurodai," Organic Letters, 2008, vol. 10, No. 3, pp. 489-491.
Smith, III, et al., "Total Synthesis of (−)-Aplaminal," Organic Letters, 2008, vol. 10, No. 19, pp. 4363-4365.
Jul. 18, 2013 International Search Report issued in International Application No. PCT/CN2013/073959.
Oct. 14, 2014 International Preliminary Report on Patentability issued in International Application No. PCT/CN2013/073959.

*Primary Examiner* — Bruck Kifle
(74) *Attorney, Agent, or Firm* — Oliff PLC

(57) ABSTRACT

The present invention relates to a compound [4-(2-amino-10-methyl-4-oxo-6,7,8,9-tetrahydro-4a,7-cycloimino-pyrimido[4,5-b][1,4]diazepine-5(4H)-yl)benzoyl]-glutamate (JK12A for short) with the structure in Formula I. The present invention also relates to the crystal form and salt of the compound JK12A, and preparation method and applications thereof. The compound JK12A of the present invention can be used to prepare drugs as an active ingredient for medicament or food additives.

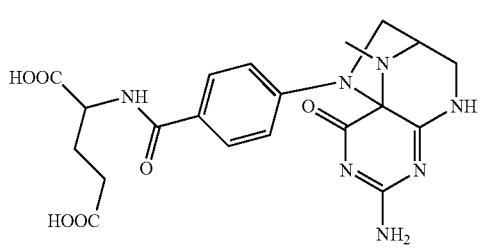

I

26 Claims, 11 Drawing Sheets

Figrue 10

COMPOUND JK12A AND PREPARATION THEREOF

TECHNICAL FIELD

The present invention relates to the field of heterocyclic compound (CO7D), wherein, the heterocyclic compound contains two or more heterocyclic rings, and nitrogen is the only heterocyclic atom of the identical cyclic system, including at least a hexatomic ring with at least one nitrogen atom (471/00). In particular, the present invention relates to a compound [4-(2-amino-10-methyl-4-oxo-6,7,8,9-tetrahydro-4a,7-imine-pyrimido[4,5-b][1,4]diazepine-5(4H)-yl)benzoyl]-glutamic acid, as well as its crystal form, a preparation method and applications.

BACKGROUND ART

The compound with triazabicyclo[3,2,1]octane structure has attracted great attention from chemists and medical experts because of its unique molecular structure.

Aplaminal is the first compound that is found to have triazabicyclo[3,2,1

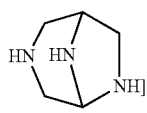

octane structure, and was first separated by Takeshi Kuroda and Hideo Kigoshi et al. from Aplysia (Varria) kurodai in the year of 2008 (Org. Lett., Vol. 10, No. 3, p489-491, 2008). Its specific structure is as follows:

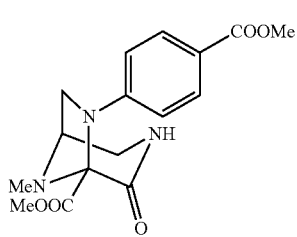

The literature characterizes the structure of Aplaminal through NMR and single crystal X-ray diffraction. It is reported that Aplaminal has the cytotoxicity against HeLa S3 cells ($IC_{50}$=0.51 ug/mL). More clinical trials are still being researched. The preparation of Aplaminal through biological extraction involves extremely high cost and produces a very low yield. Generally, only 2 mg of Aplaminal can be extracted from 18 kg of aplysia. Therefore, Amos B. Smith III and Zhuqing Liu et al. (Org. Lett., Vol. 10, No. 19, p4363-4365, 2008) prepared Aplaminal through synthesis with N-Boc-(D)-serine as the raw material in 9 reaction processes, including hydroxyl protection, condensation, reduction, etc., obtaining a yield of 17%. The specific reaction process is as follows:

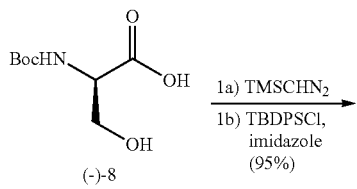

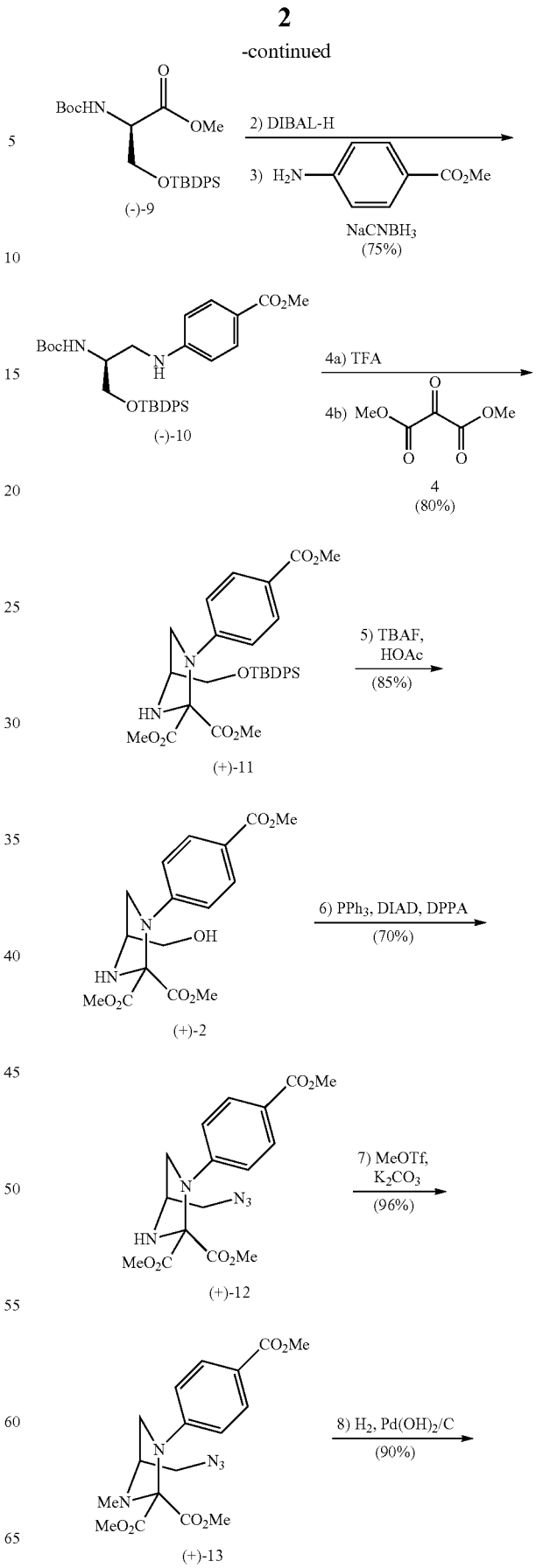

-continued

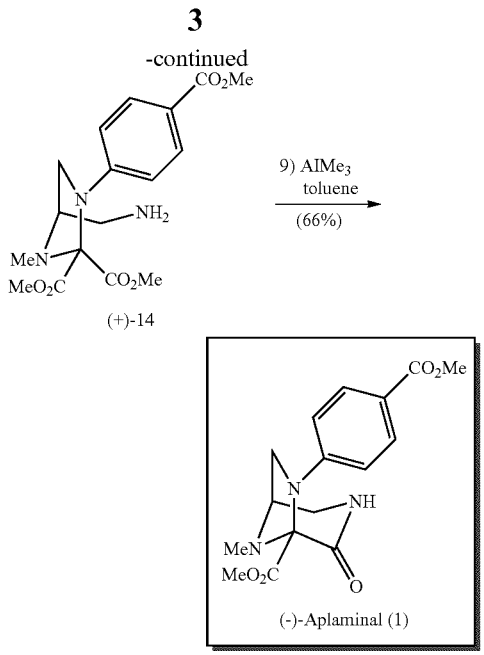

(+)-14

(-)-Aplaminal (1)

However, it is also very difficult to synthesize the compound with a triazabicyclo[3,2,1]octane structure. The above synthetic method of Aplaminal suffers from redundant reaction processes; expensive reagents such as diisobutylaluminum hydride (Dibal-H), Pd and Pt; difficult pilot process control; less safety and low yield; and is also not applicable for industrial production.

At present, there are many reports of other triazacyclo compounds. The patent document CN1864663 discloses the pharmaceutical compositions of 5,7,14-triazatetracyclo [10.3.1.0(2,11).0(4,9)]-hexadeca-2(11)3,5,7,9-pentaene. The patent document CN102282148A discloses 11-(2-pyrrolidin-1-yl-ethoxy)-14,19-dioxa-5,7,26-triazatetracyclo [19.3.1.1(2,6).1(8,12)]heptacosa-1(25),2(26),3,5,8,10,12 (27),16,21,23-decaene citrate salt. The patent document CN1509288 discloses the citrate salt of 5,8,14-triazatetracyclo[10.3.1.02,11.04,9]-hexadeca-2(11),3,5,7,9-pentaene. The patent document CN1509174 discloses the tartrate salt of 5,8,14-triazatetracyclo[10.3.1.02,11.04,9]-hexadeca-2(11), 3,5,7,9-pentaene. The patent document CN1589148 discloses the succinic acid salts of 5,8,14-triazatetracyclo [10.3.1.0.2, 10.04,8]-hexadeca-2(11),3,5,7,9-pentaene and pharmaceutical compositions thereof. These patent documents all disclose such a chemical structure with triazatetracyclo.

Through careful research, the inventor has unexpectedly developed a simple, feasible and economic method of preparing a novel compound of triazabicyclo[3,2,1]octane structure using 5-methyltetrahydrofolate as the raw material. This compound has a significant effect on inhibiting T lymphocyte proliferation.

SUMMARY OF THE INVENTION

The first object of the present invention is to provide a novel compound of triazabicyclo[3,2,1]octane and characterize its structure. The chemical name of the compound is [4-(2-amino-10-methyl-4-oxo-6,7,8,9-tetrahydro-4a,7-imine-pyrimido[4,5-b][1,4]diazepine-5(4H)-yl)benzoyl]-glutamic acid, hereinafter referred to as JK12A. The second object of the present invention is to provide a crystal form of the above compound JK12A.

The third object of the present invention is to provide a preparation method of the above compound JK12A.

The fourth object of the present invention is to provide applications of the above compound JK12A.

Therefore, the present invention proposes the compound JK12A with the following structural formula:

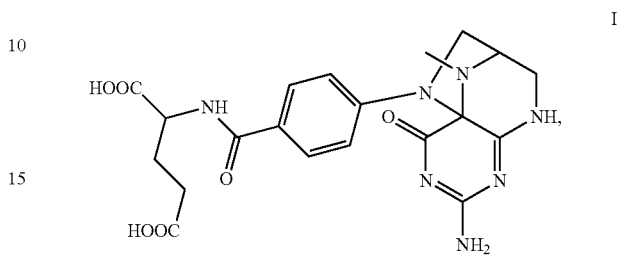

I or a stereomer of the compound JK12A.

The present invention proposes the crystal of the compound JK12A.

The present invention proposes a pharmaceutically acceptable salt of the compound JK12A or a stereomer of the salt, wherein the salt is a crystallized salt.

The present invention also provides the X-ray diffraction pattern of the crystal form I of the compound JK12A with Cu-Ka radiation, and with diffraction peaks at 2θ angle expressed in terms of degrees at 13.3±0.2, 14.0±0.2, 16.9±0.2, 19.1±0.2, 24.4±0.2 and 27.6±0.2. Furthermore, the present invention also provides the X-ray diffraction pattern of the crystal form I of the compound JK12A with Cu-Ka radiation, having diffraction peaks at 2θ angle expressed in terms of degrees at 13.3, 14.0, 16.9, 19.1, 24.4 and 27.6. The X-ray diffraction pattern of the crystal form I of the compound JK12A is shown in FIG. 11.

The present invention also provides the X-ray diffraction pattern of the crystal form II of the compound JK12A with Cu-Ka radiation, and with diffraction peaks at 2θ angle expressed in terms of degrees at 6.8±0.2, 12.2±0.2, 13.7±0.2, 15.9±0.2, 18.4±0.2 and 23.0±0.2.

Furthermore, the present invention also provides the X-ray diffraction pattern of the crystal form II of the compound JK12A with Cu-Ka radiation, having diffraction peaks at 2θ angle expressed in terms of degrees at 6.8, 12.2, 13.7, 15.9, 18.4 and 23.0. The further X-ray diffraction pattern of the crystal form II of the compound JK12A is shown in FIG. 12.

The present invention provides a preparation method of the compound JK12A, comprising the process of oxidizing 5-methyltetrahydrofolate.

The present invention provides a preparation method of the crystal form I of the compound JK12A, comprising the following steps:
a) Adding the 5-methyltetrahydrofolate into polar medium;
b) Regulating the pH with alkali to 6~8;
c) Adding an oxidizing agent with stirring;
d) Regulating the pH with acid to 3~5;
e) Crystallization.

The present invention also provides a preparation method of the crystal form II of the compound JK12A, comprising crystallization of the compound JK12A in polar medium through ultrasonication at pH-≥3. The polar medium can be water or a mixture of water and a polar water-miscible organic solvent.

Furthermore, the present invention provides a preparation method of the crystal form II of the compound JK12A, comprising the following steps:

a) Adding the compound JK12A into polar medium;

b) Regulating the pH with alkali to 6~10, until the solid is dissolved;

c) Crystallization through ultrasonication and regulating the pH with acid to 3~6. Purity of the crystal form I and II of the compound JK12A prepared from the above method can reach above 98.0%.

The present invention also provides a method for converting the compound JK12A to 5-methyltetrahydrofolate comprising reducing the compound JK12A to 5-methyltetrahydrofolate.

The present invention also provides a method for converting the compound JK12A to 5-methyltetrahydrofolate. An embodiment of the conversion method comprises dissolving the compound JK12A in water in the presence of alkali, then reacting with a reducing agent to obtain 5-methyltetrahydrofolate.

The present invention also provides applications of the compound JK12A such as for preparing drugs, and serving as an active ingredient in medications or food additives.

DETAILED DESCRIPTION OF THE INVENTION

Figure 1:
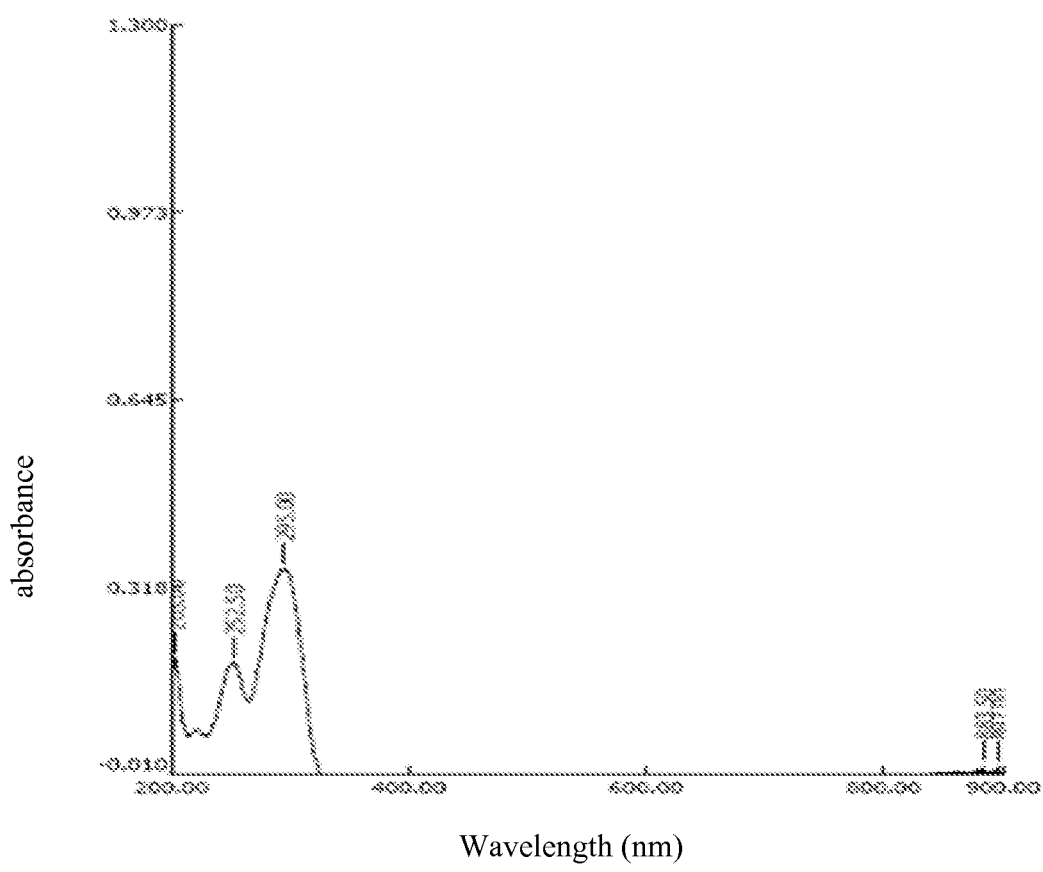
FIG. 1: UV spectrum of JK12A.

In order to better understand the technical scheme of the present invention, a detailed description of the preferred embodiments is presented to further illustrate the technical scheme of the present invention, but is not intended to restrict the present invention.

The compound JK12A referred to in the present invention can be characterized by various means.

The compound JK12A, is characterized in that it is synthesized through oxidation of 5-methyltetrahydrofolate. Where, the chemical name of the 5-methyltetrahydrofolate is N-[4-[[(2-amino-1,4,5,6,7,8,-hexahydro-4-oxo-5-methyl-6-pteridinyl)methyl]amino]benzoyl]-L-glutamic acid. Please refer to patent documents CN1122337A, CN92100247.5, CN200910134474.4, CN200610041541.4, CN00108884.X and GR3029552T3 for the characteristics of 5-methyltetrahydrofolate, the technical disclosures of which are incorporated herein by reference in their entireties. Therefore, the present invention proposes the following structural formula for 5-methyltetrahydrofolate:

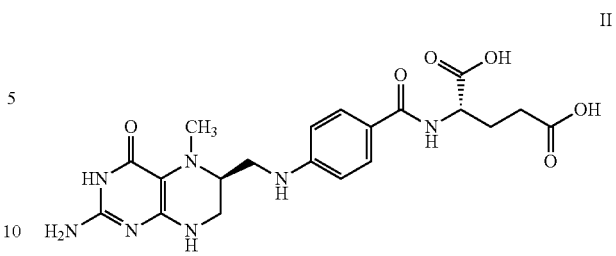

II

In the invention, 5-methyltetrahydrofolate is oxidized with an oxidizing agent. As described below, the oxidizing agent may be air, or oxygen, or hydrogen peroxide.

The compound JK12A, is prepared with the following method:

a) Dissolving 5-methyltetrahydrofolate in polar medium in the presence of alkali;

b) Generating the compound JK12A through reaction with the oxidizing agent;

c) Separating the compound JK12A from solution with acid,

Wherein, nitrogen or inert gas protection may be used in step a); nitrogen is preferred; 5-methyltetrahydrofolate solution is regulated with alkali to pH value of 6~8, until the solid is dissolved. In step b), high active surfactant may be used as a catalyst and/or ultrasonication may be used; the oxidizing agent is preferably air, or oxygen, or hydrogen peroxide. In step c), the reaction solution is regulated to pH 3~5 preferably with acid. After precipitation, the solid is filtered, washed and dried. The preparation process is carried out under normal pressure and at normal temperature. The duration of each step is determined, as necessary, according to the amount of the raw material (5-methyltetrahydrofolate), alkali and acid, etc. The compound JK12A, also having the molecular structure as follows:

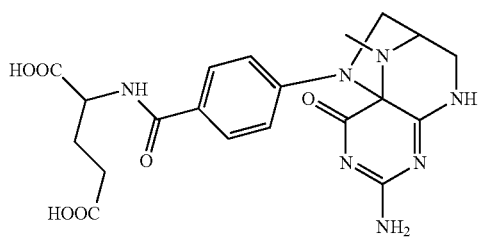

I

The present invention also relates to a variety of stereomers of the compound JK12A, such as [4-((4aS, 7R)-2-amino-10-methyl-4-oxo-6,7,8,9-tetrahydro-4a,7-cycloimino-pyrimido[4,5-b][1,4]diazepine-5(4H)-yl)benzoyl]-1,-glutamic acid, [4-((4aS, 7S)-2-amino-10-methyl-4-oxo-6,7,8,9-tetrahydro-4a,7-cycloimino-pyrimido[4,5-b][1,4]diazepine-5(4H)-yl)benzoyl]-L-glutamic acid, [4-((4aR, 7S)-2-amino-10-methyl-4-oxo-6,7,8,9-tetrahydro-4a,7-cycloimino-pyrimido[4,5-b][1,4]diazepine-5(4H)-yl)benzoyl]-L-glutamic acid, [4-((4aR, 7R)-2-amino-10-methyl-4-oxo-6,7,8,9-tetrahydro-4a,7-cycloimino-pyrimido[4,5-b][1,4]diazepine-5(4H)-yl)benzoyl]-L-glutamic acid, etc.

JK12A in the present invention may be characterized by one or more of the following means:

UV spectrum with maximum absorption peaks at about 203.0 nm, 252.5 nm and 295.5 nm;

IR spectrum with peaks at about 3383 cm$^{-1}$, 2885 cm$^{-1}$, 1608 cm$^{-1}$, 1558 cm$^{-1}$, 1508 cm$^{-1}$, 1421 and 1321 cm$^{-1}$;

1HNMR spectrum with chemical shift of hydrogen at about 1.89, 2.04, 2.31, 3.43, 3.49, 3.86, 3.90, 3.94, 4.21, 6.48 and 7.62;
13CNMR spectrum with chemical shift of carbon at about 28.37, 31.26, 34.25, 45.18, 55.04, 55.16, 55.93, 68.80, 112.23, 129.17, 146.36, 165.58, 169.50, 171.74, 176.65, 179.29 and 182.49;
HR-MS (ESI−) spectrum with a peak at about m/z=456.163761 ([M-H]−); indicating that the molecular weight of JK12A is 457, and its elementary composition is $C_{20}H_{23}N_7O_6$.

The present invention also relates to the crystal of the compound JK12A. Through experimentation, the inventor has found two crystal forms.

The preparation method of the crystal form I of the compound JK12A crystal, comprising the following steps:
a) Adding the 5-methyltetrahydrofolate into polar medium;
b) Regulating the pH with alkali to 6~8;
c) Adding an oxidizing agent with stirring;
d) Regulating the pH with acid to 3~5;
e) Crystallization.

Preferably, in step a), the polar medium is water or a mixture of water and a water-miscible organic solvent. This method does not have specific requirements for the amount of the polar medium. The 5-methyltetrahydrofolate is selected from (6S)-5-methyltetrahydrofolate, (6R)-5-methyltetrahydrofolate and (6R, S)-5-methyltetrahydrofolate, and is preferably (6S)-5-methyltetrahydrofolate.

In step b), the alkali is an organic alkali or inorganic alkali that can form a salt with 5-methyltetrahydrofolate, wherein, the inorganic alkali is selected from alkali of alkalis or alkaline earth, carbonate and bicarbonate; the organic alkali is selected from ammonia, amine, pyridine and piperazine; preferably potassium hydroxide, sodium hydroxide, calcium hydroxide, magnesium hydroxide, potassium carbonate, sodium carbonate, potassium bicarbonate, sodium bicarbonate, ammonia, monomethylamine, 4-dimethylpyridine, and piperazine. The alkali may be directly added, or added in the form of solution (aqueous solution for instance). The pH value of the solution is generally regulated with alkali generally to 6.0~8.0, preferably 7.0~7.5.

In step c), the oxidizing agent is air, or oxygen, or hydrogen peroxide.

Preferably, a step of adding high active surfactant before the step c) can be included. The high active surfactant is selected from active carbon, active silica gel and active aluminum oxide, and is preferably active carbon. Wherein, the use level of the high active surfactant is 0.05~10 times as much as the mass of 5-methyltetrahydrofolate, preferably 0.5~2 times, and more preferably 0.5~1 times. More preferably, the high active surfactant is added between the step b) and step c), that is, the oxidizing agent is added immediately after adding the high active surfactant. The stirring is preferably terminated after the reaction of the raw material 5-methyltetrahydrofolate is over, as indicated by HPLC, lasting for generally more than 10 hours, and preferably 12-24 hours.

In step d), the acid is organic acid or inorganic acid. Preferably, the inorganic acid is selected from hydrochloric acid, sulfuric acid and hydrobromic acid; the organic acid is selected from formic acid, acetic acid and phenylmethanesulfonic acid. The pH value of the solution is preferably regulated with acid to 4~5. It is understandable that after crystallization, steps such as filtration, washing, drying and the like can be carried out.

The main peaks of the X-ray diffraction pattern in terms of 2θ and distance d measured through CuKα radiation (within the error range) of crystal form I are listed as follows:

TABLE 1

Characteristic peaks of the X-ray diffraction pattern of the crystal form I

| 2θ (±0.2) | d (Å) (±0.2) |
|---|---|
| 13.3 | 6.7 |
| 14.0 | 6.3 |
| 16.9 | 5.2 |
| 19.1 | 4.6 |
| 24.4 | 3.6 |
| 27.6 | 3.2 |

The crystal form II of the compound JK12A, wherein, the compound JK12A is crystallized with the aid of ultrasonication in polar medium at pH≥3. Preferably, the polar medium is water or a mixture or water and a polar water-miscible organic solvent. Furthermore, the preparation method of the crystal form II of the compound JK12A, comprises the following steps:
a) Adding the compound JK12A into polar medium;
b) Regulating the pH with alkali to 6~10, until the solid is dissolved;
c) Crystallization through ultrasonication and regulating the pH with acid to 3~6.

In step a), the compound JK12A may be amorphous or crystal form I. The polar medium is water or a mixture of water and a polar water-miscible organic solvent. In step b), the alkali is organic alkali or inorganic alkali. Preferably, the inorganic alkali is selected from potassium hydroxide, sodium hydroxide, calcium hydroxide, magnesium hydroxide, potassium carbonate, sodium carbonate, potassium bicarbonate and sodium bicarbonate; the organic alkali is selected from ammonia, monomethylamine, 4-dimethylpyridine and piperazine. The alkali may be directly added, or added in the form of solution (aqueous solution for instance). The pH of the solution is regulated with the alkali preferably to 7.0~8.0, and more preferably 7.0~7.5.

In step c), the acid is organic acid or inorganic acid. Preferably, the inorganic acid is selected from hydrochloric acid, sulfuric acid and hydrobromic acid; the organic acid is selected from formic acid, acetic acid and phenylmethanesulfonic acid. A pH value of the solution is preferably regulated with acid to 3~4. In the step b), ultrasonication may be used to facilitate fast dissolution of the compound JK12A. In the step c), ultrasonication is used to facilitate formation of the crystal form II. The duration of ultrasonication is determined as necessary, and may stop after enough solid precipitates.

The main peaks of the X-ray diffraction pattern in terms of 2θ and distance d measured through CuKα radiation (within the error range) of crystal form II are listed as follows:

TABLE 2

Characteristic peak of the X-ray diffraction pattern of the crystal form II

| 2θ (±0.2) | d (Å) (±0.2) |
|---|---|
| 6.8 | 13.0 |
| 12.2 | 7.3 |
| 13.7 | 6.5 |
| 15.9 | 5.6 |
| 18.4 | 4.8 |
| 23.0 | 3.8 |

The present invention also relates to a method for converting the compound JK12A to 5-methyltetrahydrofolate, comprising reducing the compound JK12A to 5-methyltetrahydrofolate. The method may also be used for purification of 5-methyltetrahydrofolate. Crude product of 5-methyltetrahydrofolate is oxidized to form JK12A, which is reduced to 5-methyltetrahydrofolate after crystallization. The 5-methyltetrahydrofolate is obtained with significantly improved chemical purity and optical purity. Therefore, one of the applications of the compound JK12A of the present invention is to prepare and purify 5-methyltetrahydrofolate.

The present invention relates to a preparation method of 5-methyltetrahydrofolate, wherein, the compound JK12A is reduced to 5-methyltetrahydrofolate.

Preferably, the preparation method of 5-methyltetrahydrofolate comprises: first dissolving the compound JK12A in water in the presence alkali, then adding the reducing agent, and obtaining 5-methyltetrahydrofolate through separation. Wherein, the reducing agent is preferably borohydride, or reducing gas, or sulfhydryl compound. The borohydride is selected from sodium borohydride, potassium borohydride and potassium tri-tert-butylborohydride; the reducing gas is selected from $H_2$ and borane; the sulfhydryl compound is selected from mercaptoethanol, cysteine and mesna. The separation step refers to separating 5-methyltetrahydrofolate from solution and is a prior art that may be referred to in relevant reference documents cited hereinbefore.

The alkali is an inorganic alkali or organic alkali that can form a salt with 5-methyltetrahydrofolate. The inorganic alkali is selected from alkali of alkalis or alkaline earth, carbonate and bicarbonate; the organic alkali is selected from ammonia, amine, pyridine and piperazine; preferably: potassium hydroxide, sodium hydroxide, calcium hydroxide, magnesium hydroxide, potassium carbonate, sodium carbonate, potassium bicarbonate, sodium bicarbonate, ammonia, monomethylamine, 4-dimethylpyridine and piperazine. The alkali may be directly added, or added in the form of solution (aqueous solution for instance). The present invention also relates to an acceptable salt of the compound JK12A, which is selected from alkali metal salt or alkaline earth metal salt, preferably potassium salt, sodium salt, calcium salt, magnesium salt, barium salt and strontium salt, and more preferably calcium salt.

The present invention also relates to a preparation method of the calcium salt of the compound JK12A, comprising the following steps:
a) Adding the compound JK12A into polar medium;
b) Regulating the pH with alkali to 7~8, until the solid is dissolved;
c) Adding calcium chloride;
d) Solid precipitation through ultrasonication, then filtration, washing and drying;

In step a), the polar medium is water or a mixture of water and a polar water-soluble organic solvent, preferably water. In step b), the alkali is an organic alkali or inorganic alkali. Preferably, the inorganic alkali is selected from potassium hydroxide, sodium hydroxide, calcium hydroxide, magnesium hydroxide, potassium carbonate, sodium carbonate, potassium bicarbonate and sodium bicarbonate; the organic alkali is selected from ammonia, monomethylamine, 4-dimethylpyridine and piperazine.

The compound JK12A is used as an active ingredient of drugs in drug preparation. The immune bioactivity experiment in Example 16 shows that the compound JK12A can be used to prepare drugs, and may also be used to prepare food additives.

The pharmaceutical preparations or compositions in the present invention contain the above compound JK12A or salt thereof. The compound JK12A or salt thereof prepared with the method in the present invention is ideal for pharmaceutical preparations. The pharmaceutical preparations in the present invention may contain one or more excipients besides active ingredients. The excipients are added to pharmaceutical preparations for various purposes. The above preparations may be prepared with the prior art in this field.

The compound JK12A prepared in the present invention is analyzed as follows:

1. Ultraviolet (UV) Analysis:
Instrument model: TU-1901, Beijing Purkinje General Instrument Co., Ltd, TU-1901
Sample concentration: 0.02366 mg/mL
Solvent: Methanol
Scan range: 200.00-900.00 nm
Scanning interval: 0.50 nm
Test result: UV spectrum of this product shows that there are maximum absorption at 203.0 nm, 252.5 nm and 295.5 nm, respectively corresponding to absorption of —C=O and K band of the benzene ring. UV absorption spectrum is shown in FIG. 1.

Figure 2:
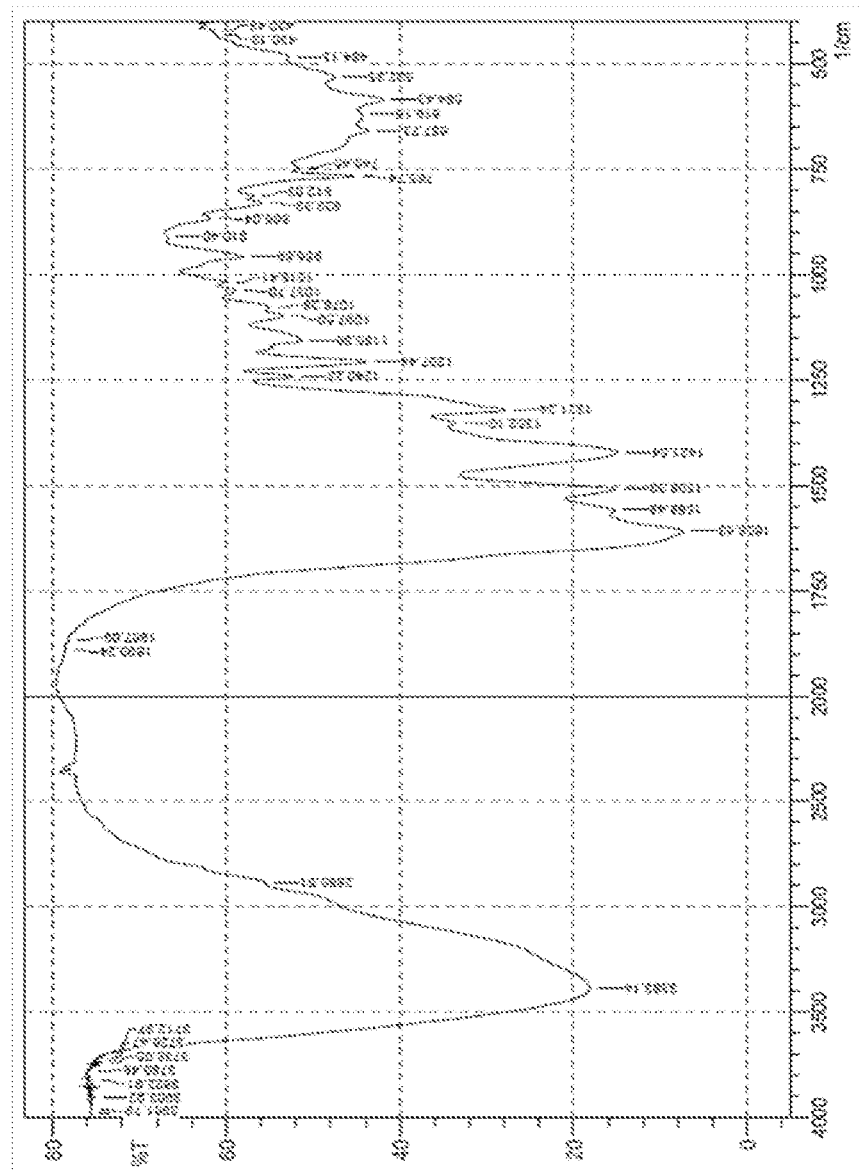
FIG. 2: IR spectrum of JK12A.

2. IR Analysis:
Instrument model: Shimadzu, FTIR Presitage 21
Test conditions: KBr tabletting method
Test result: Main absorption peaks and corresponding groups are shown in Table 1. The IR absorption spectrum is shown in FIG. 2.

TABLE 3

Main IR absorption peaks of the compound JK12A

| Absorption peak ($cm^{-1}$) | Vibration | Corresponding group | Absorption peak intensity |
|---|---|---|---|
| 3383 | $\upsilon NH_2 \upsilon OH \upsilon NH$ | —$NH_2$ —OH —NH | s |
| 2885 | $\upsilon CH$ | —CH—, —$CH_2$ | w |
| 1608 | $\upsilon C=O$ | —C=O | s |
| 1558 | $\upsilon C=N$ | —C=N | s |
| 1508, 1421 | $\upsilon C=C$ | —C=C | s |
| 1321 | $\upsilon C$—N | —C—N | m |

Figure 3:
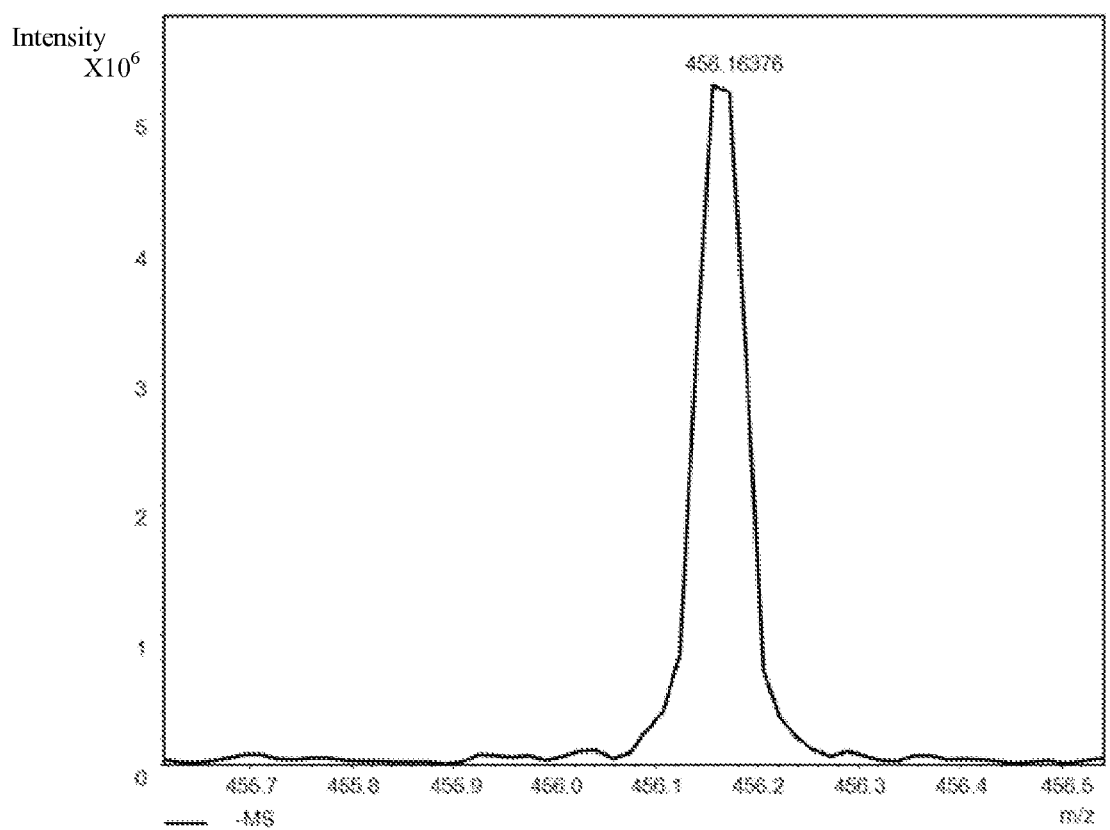
FIG. 3: High resolution mass spectrum of JK12A.
Figure 4:
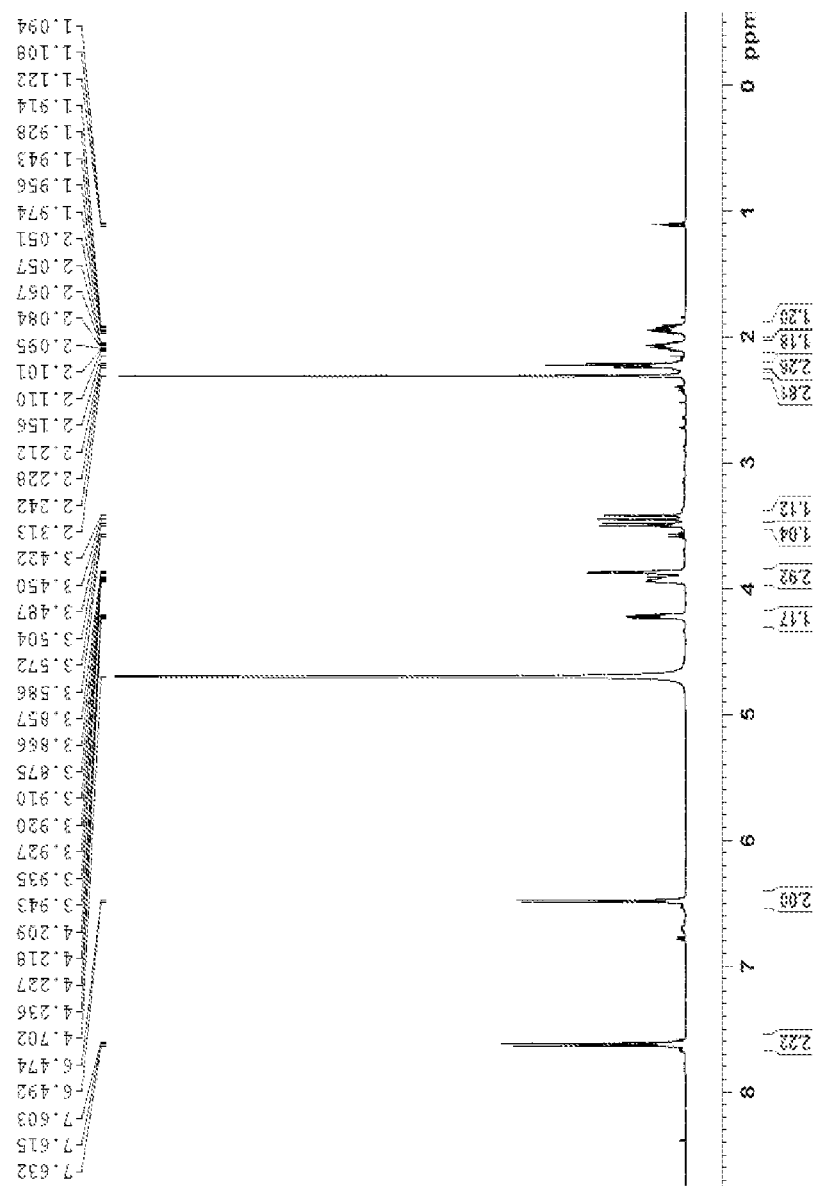
FIG. 4: H-NMR spectrum of JK12A.
Figure 5:
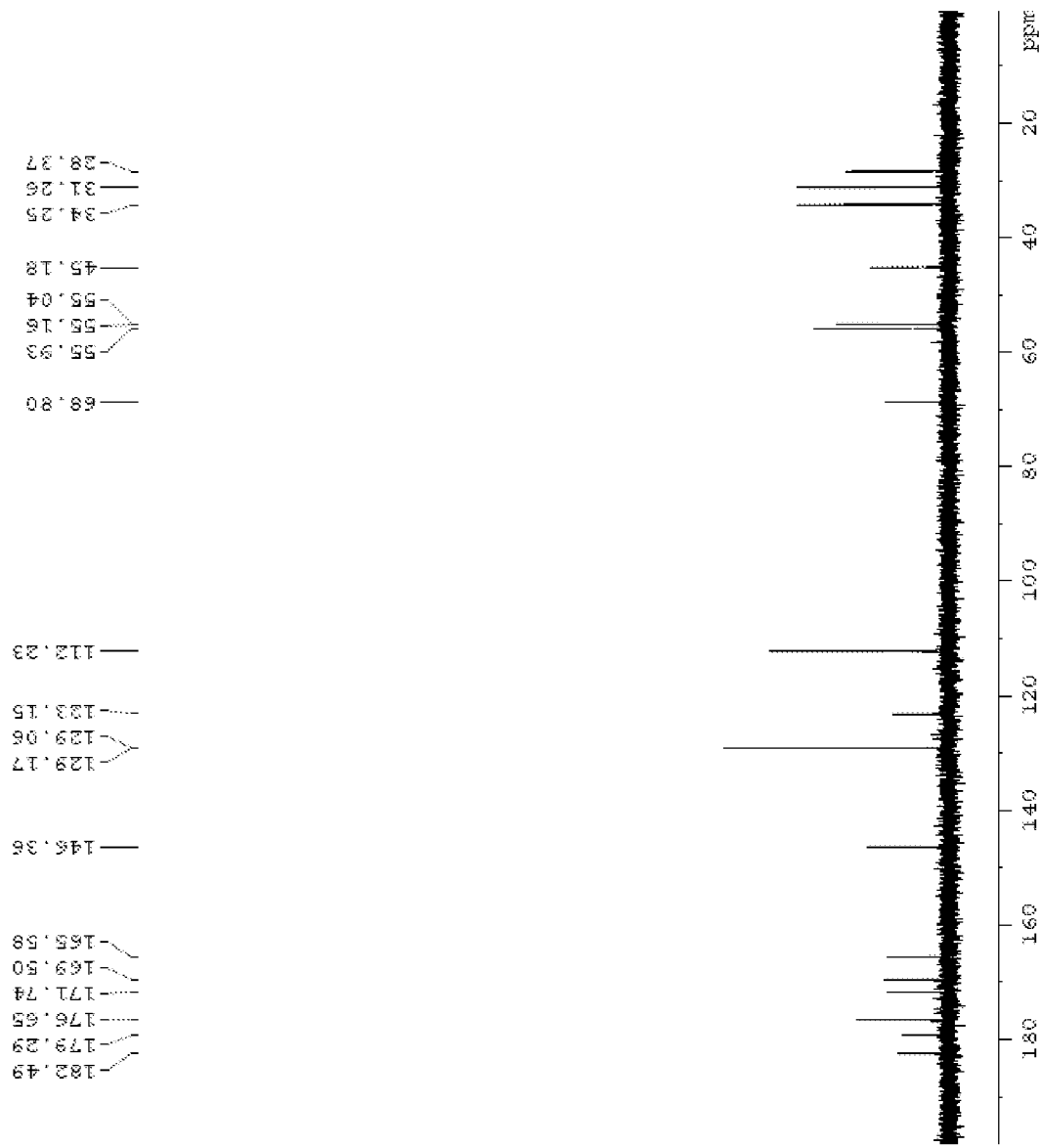
FIG. 5: C-NMR spectrum of JK12A.
Figure 6:
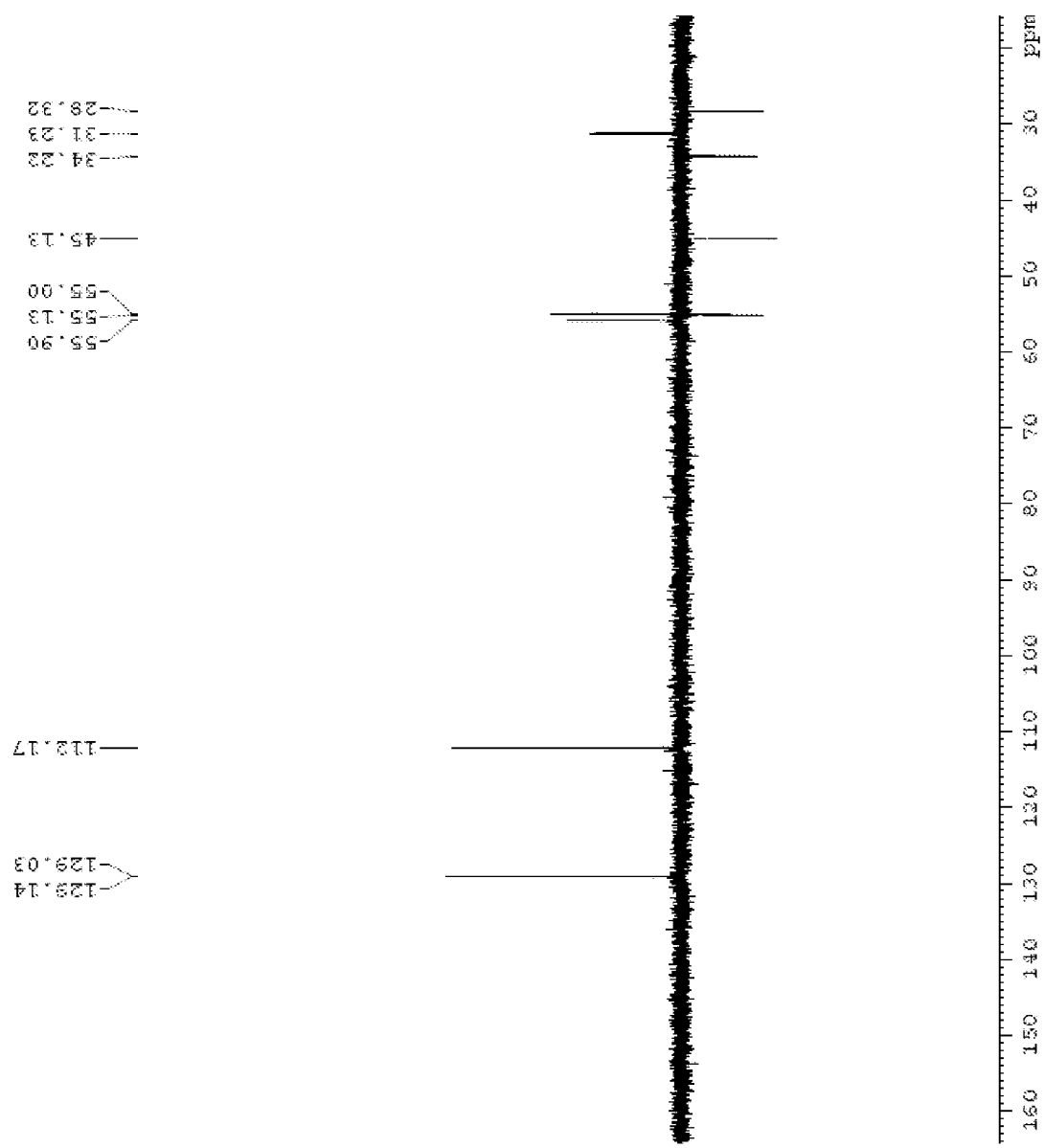
FIG. 6: DEPT135-NMR spectrum of JK12A.
Figure 7:
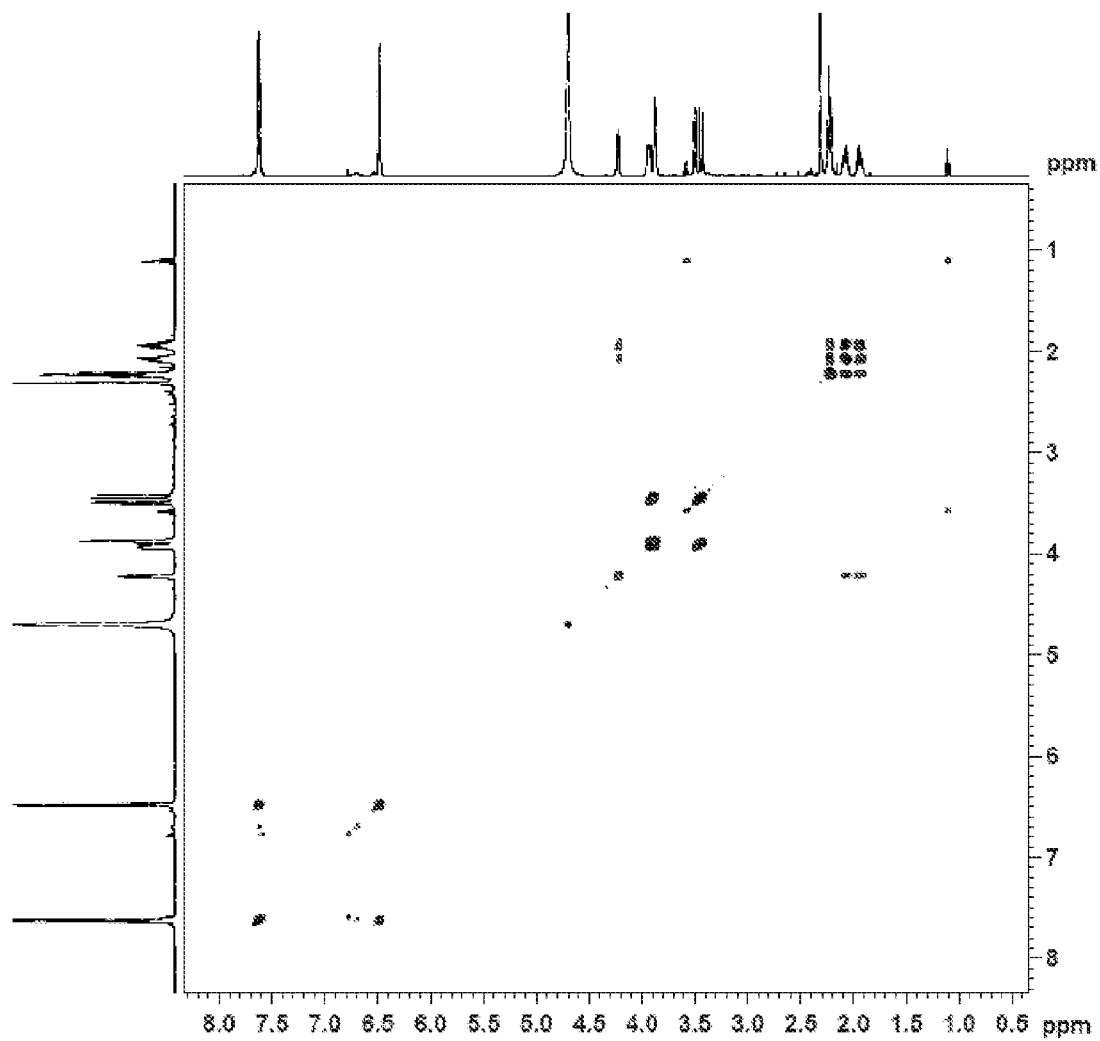
FIG. 7: $^1$H-$^1$HCOSY-NMR spectrum of JK12A.
Figure 8:
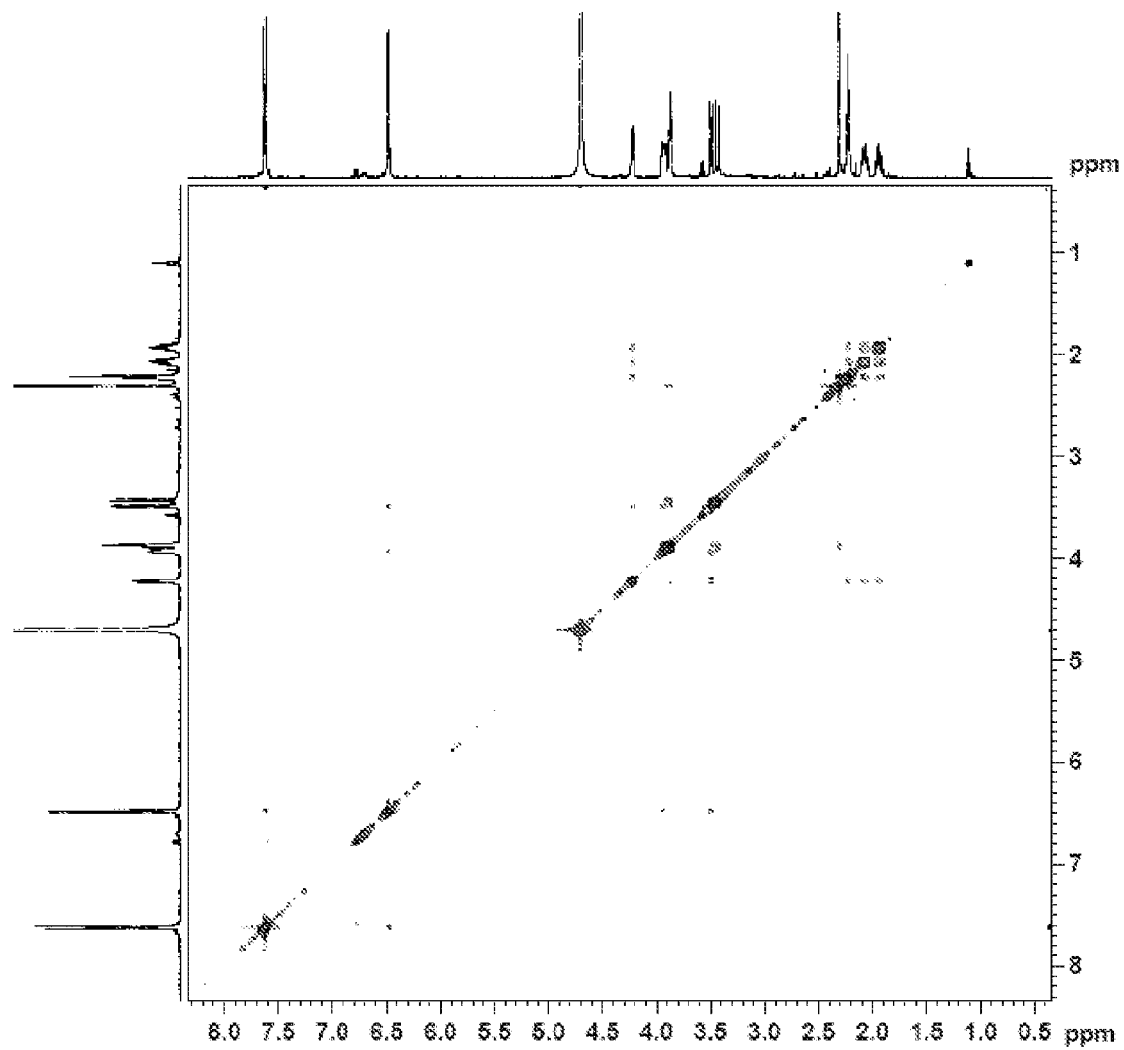
FIG. 8: $^1$H-$^1$HNOESY-NMR spectrum of JK12A.
Figure 9:
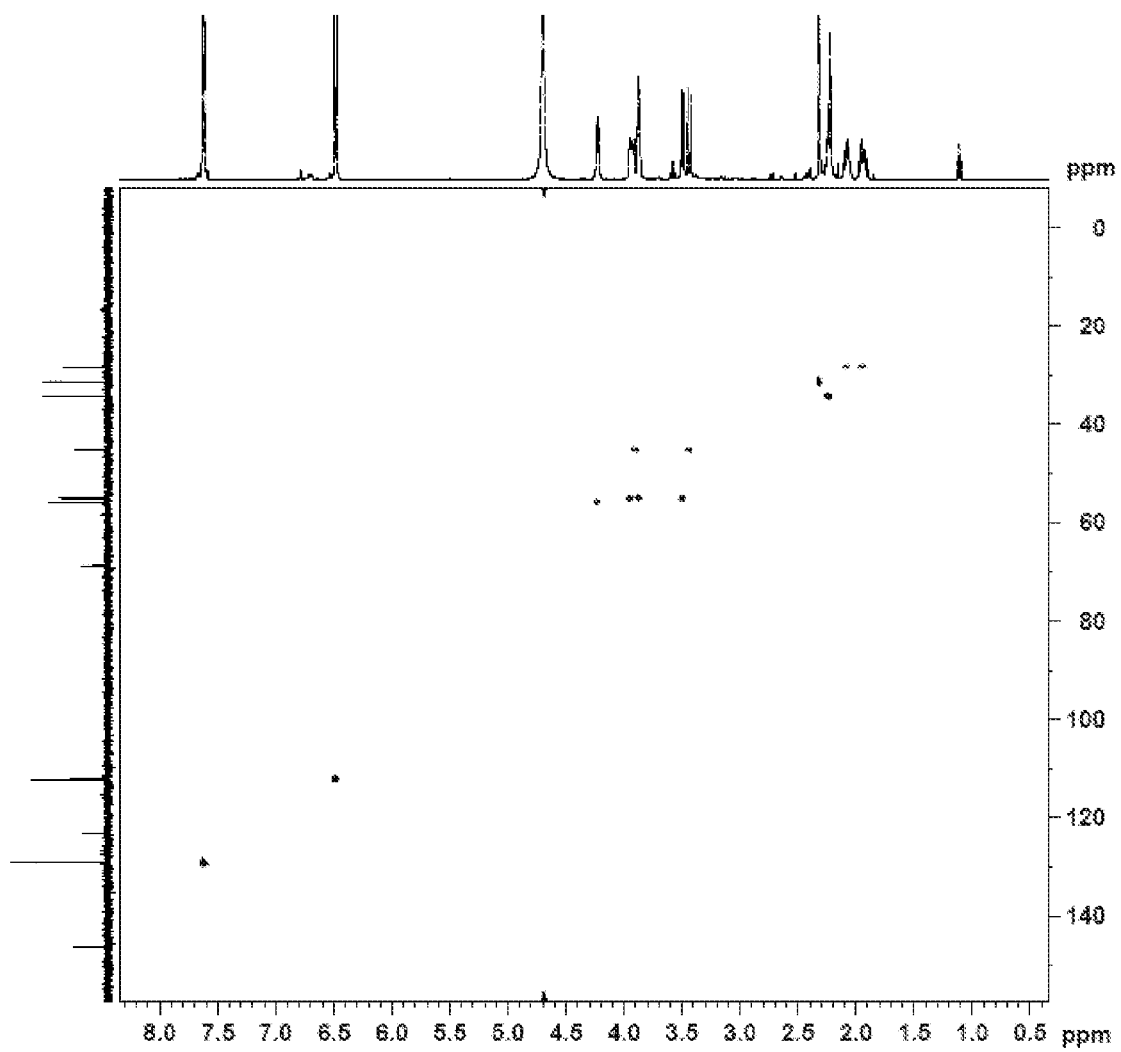
FIG. 9: HSQC-NMR spectrum of JK12A.
Figure 10:
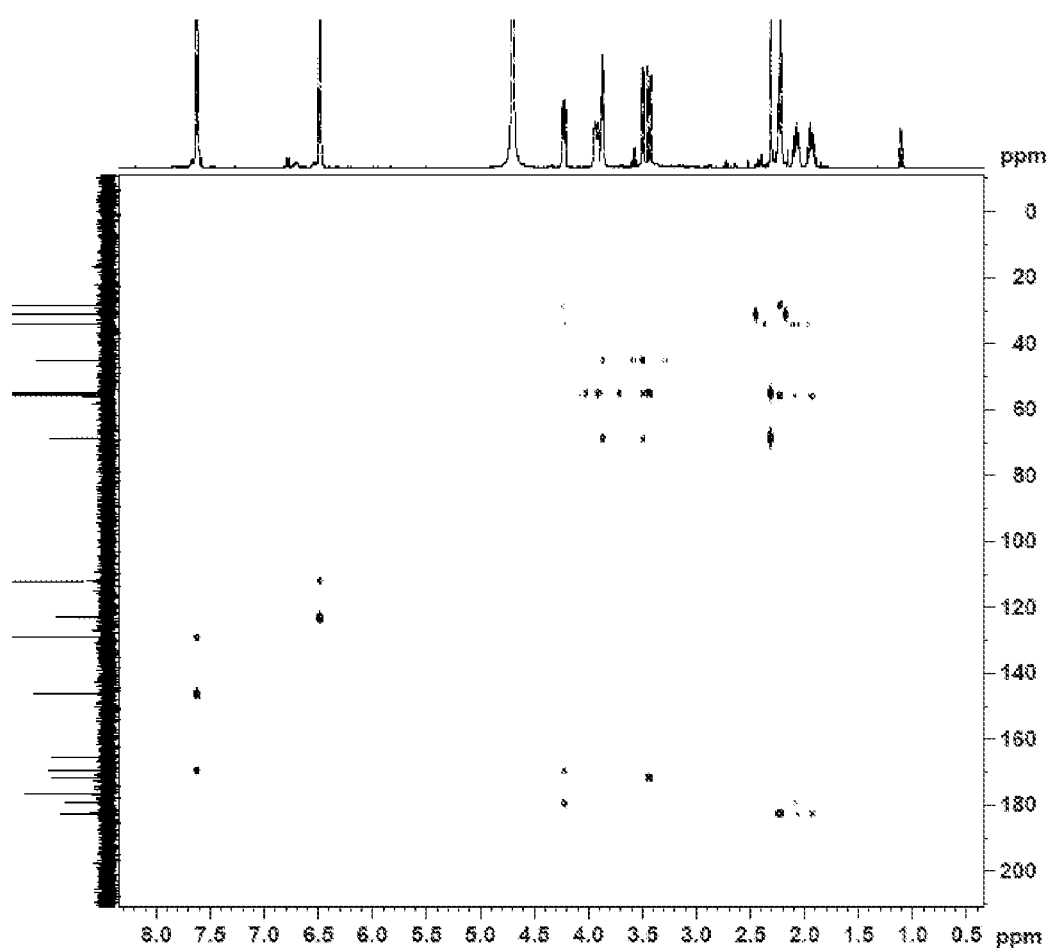
FIG. 10: HMBC-NMR spectrum of JK12A.
Figure 11:
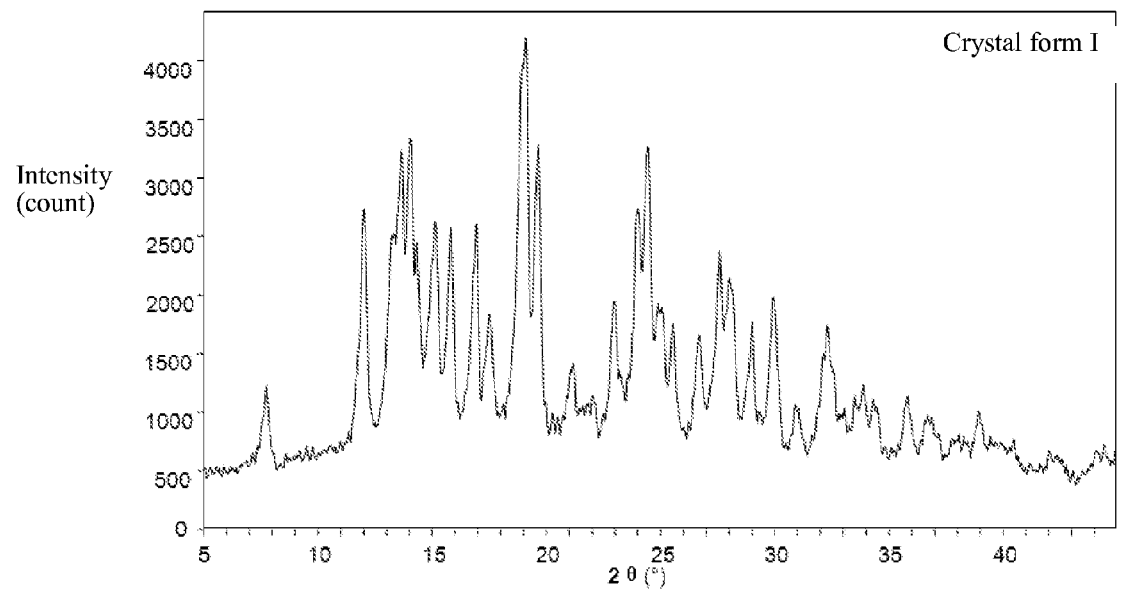
FIG. 11: X-ray diffraction pattern of the crystal form I of JK12A.
Figure 12:
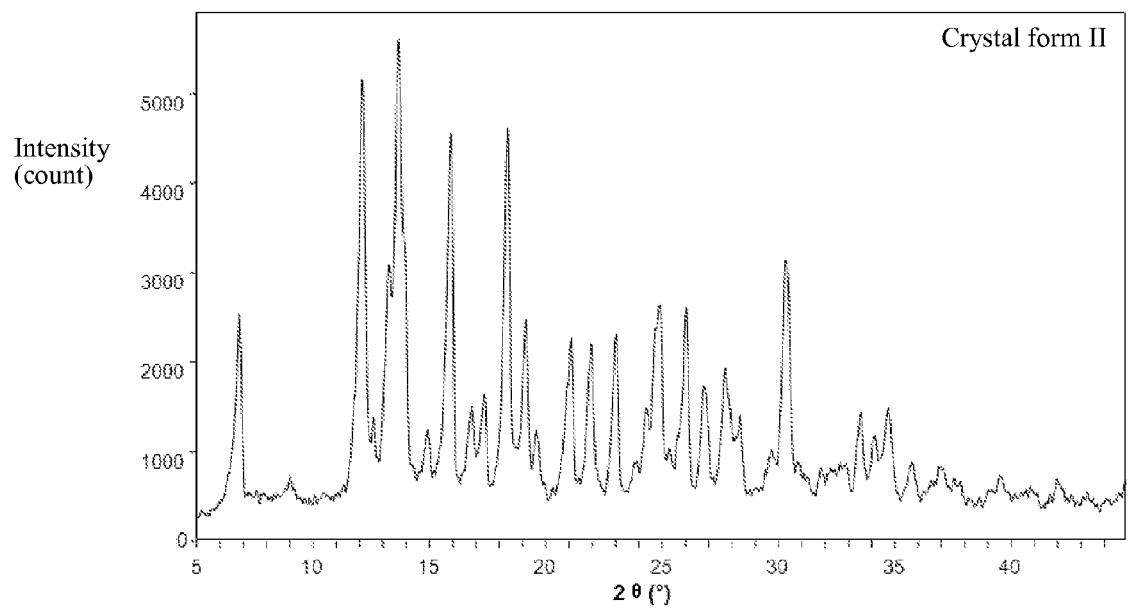
FIG. 12: X-ray diffraction pattern of the crystal form II of JK12A.

3. High Resolution Mass Spectrometry (HR-MS):
Instrument model: Bruker Daltonics, Inc., APEX III 7.0TESLAFTMS
Test result: Elementary composition of this product is measured using high resolution mass spectrometry. A peak at 456.16376 is obtained through detection in the anionic mode of ESI-MS/MS, showing that elementary composition of this product is $C_{20}H_{23}N_7O_6$. Data list is shown in Table 2, and the mass spectrum is shown in FIG. 3.

TABLE 4

High resolution elementary composition analysis data list

| Measured value | Theoretical value | Deviation (mDa) | Precision (ppm) | Elementary composition |
|---|---|---|---|---|
| 456.16376 | 456.16371 | −0.05 | −6.01 | $C_{20}H_{23}N_7O_6$ |

4. NMR Analysis
Instrument model: Bruker, AVANCE III500 MHz UltraShield-Plus™ digital NMR spectrometer
Solvent: $D_2O$
Test items:
$^1H$-NMR, $^{13}C$-NMR, DEPT135, $^1H$-$^1H$COSY, $^1H$-$^1H$NOESY, HSQC, HMBC
Test result: NMR spectrum is shown in FIGS. 4-10. Corresponding groups are listed in Table 3 and Table 4.

TABLE 5

Chemical shift of $^1$H

| Chemical shift δ(ppm) | Diversity | Proton number | Corresponding group | $^1$H-$^1$H COSY Relative absorption | $^1$H-$^1$H NOESY Relative absorption |
|---|---|---|---|---|---|
| 7.62 | d, J = 8.8 Hz | 2H | H-16,18 | H-15,19 | H-16,18 |
| 6.48 | d, J = 8.8 Hz | 2H | H-15,19 | H-16,18 | H-15,19,9,9' |
| 4.21 | dd, J = 9.0, 4.6 Hz | 1H | H-22 | H-23,23' | H-23,23',24 |
| 3.94 | m | 1H | H-6 | H-7',9' | |
| 3.90 | m | 1H | H-7 | H-7'.6 | |
| 3.86 | m | 1H | H-9 | H-9',6 | |
| 3.49 | d, J = 8.4 Hz | 1H | H-9' | H-9,6 | H-9,6 |
| 3.43 | d, J = 14.1 Hz | 1H | H-7' | H-7,6 | H-7,6 |
| 2.31 | s | 3H | H-11 | | H-6 |
| 2.22 | t, J = 7.9 Hz | 2H | H-24 | H-23,23' | H-22,23,23' |
| 2.04-2.11 | m | 1H | H-23 | H-23',24,22 | H-23',24,22 |
| 1.89-1.97 | m | 1H | H-23' | H-23,24,22 | H-23,24,22 |

TABLE 6

Chemical shift of $^{13}$C

| Chemical shift δ ppm | Carbon number | Corresponding group | DEPT135 | HSQC | HMBC |
|---|---|---|---|---|---|
| 182.49 | 1 | C-25 | C | — | H-23,23',24 |
| 179.29 | 1 | C-26 | C | — | H-22,23 |
| 176.65 | 1 | C-4 | C | — | |
| 171.74 | 1 | C-13 | C | — | H-7 |
| 169.50 | 1 | C-20 | C | — | H-16,19,22 |
| 165.58 | 1 | C-2 | C | — | — |
| 146.36 | 1 | C-14 | C | — | H-16,18 |
| 129.17 | 2 | C-16,18 | CH | H-16,18 | |
| 123.15 | 1 | C-17 | C | — | H-15,19 |
| 112.23 | 2 | C-15,19 | CH | H-15,19 | |
| 68.80 | 1 | C-12 | C | — | H-6,9',11 |
| 55.93 | 1 | C-22 | CH | H-22 | H-23,24 |
| 55.16 | 1 | C-9 | CH2 | H-9,9' | H-7 |
| 55.04 | 1 | C-6 | CH | H-6 | H-11 |
| 45.18 | 1 | C-7 | CH2 | H-7,7' | H-9 |
| 34.25 | 1 | C-24 | CH2 | H-24 | H-22,23' |
| 31.26 | 1 | C-11 | CH3 | H-11 | |
| 28.37 | 1 | C-23 | CH2 | H-23,23' | H-22,24 |

Example 1

Preparation of the Crystal Form I of JK12A

Under nitrogen protection, 5 g of 5-methyltetrahydrofolate was dissolved in 50 g of water in a reaction flask with stirring, and then regulated with saturated sodium carbonate solution to pH 7.5. After the solid was completely dissolved, 2.5 g of active carbon was added, and then sealed in an oxygen balloon overnight. After HPLC showed that the reaction of raw materials was completed, the system was filtered, and the filtrate was regulated with 50% acetic acid to pH 4.8 for crystallization. After filtration, the filter cake was respectively washed with ethanol and acetone, and then 3.0 g of yellow solid was obtained through vacuum drying with purity of 87.53%.

Example 2

Preparation of the Crystal Form I of JK12A

Under nitrogen protection, 5 g of 5-methyltetrahydrofolate was dissolved in 40 g of water in a reaction flask with stirring, and then regulated with 90% monomethylamine solution to pH 7.0. After the solid was completely dissolved, 2.5 g of active carbon was added, and then sealed in an oxygen balloon overnight. After HPLC showed that the reaction of raw materials was completed, the system was filtered, and the filtrate was regulated with 10% hydrochloric acid to pH 3.0 for crystallization. After filtration, the filter cake was respectively washed with ethanol and acetone, and then 2.5 g of yellow solid was obtained through vacuum drying with chemical purity of 97.37%.

Example 3

Preparation of the Crystal Form I of JK12A

Under nitrogen protection, 5 g of 5-methyltetrahydrofolate was dissolved in 40 g of water in a reaction flask with stirring, and then regulated with 10% sodium hydroxide solution to pH 7.5. After the solid was completely dissolved, 2.5 g of active carbon was added, and then kept open overnight. After HPLC showed that the reaction of raw materials was completed, the system was filtered, and the filtrate was regulated with 50% acetic acid to pH 4.2 for crystallization. After filtration, the filter cake was respectively washed with ethanol and acetone, and then 2.3 g of yellow solid was obtained through vacuum drying with chemical purity of 95.00%.

Example 4

Preparation of the Crystal Form I of JK12A

Under nitrogen protection, 73.3 g of 5-methyltetrahydrofolate was dissolved in 580 g of water in a reaction flask with stirring, and then regulated with 10% sodium hydroxide solution to pH 7.2. After the solid was completely dissolved, 40 g of active carbon was added, and then sealed in an oxygen balloon overnight. After HPLC showed that the reaction of raw materials was completed, the system was filtered, and the filtrate was regulated with 50% acetic acid to pH 4.0 for crystallization. After filtration, the filter cake was respectively washed with ethanol and acetone, and then 47.8 g of yellow solid was obtained through vacuum drying with chemical purity of 96.20%.

Example 5

Preparation of the Crystal Form I of JK12A

Under nitrogen protection, 10 g of 5-methyltetrahydrofolate was dissolved in 80 g of water in a reaction flask with stirring, and then regulated with 10% sodium hydroxide solution to pH 7.3. After the solid was completely dissolved, 5 g of active carbon was added, and then kept open overnight. After HPLC showed that the reaction of raw materials was completed, the system was filtered, and the filtrate was regulated with 50% acetic acid to pH 4.0 for crystallization. After filtration, the filter cake was respectively washed with ethanol and acetone, and then 6.0 g of yellow solid JK12A was obtained through vacuum drying with chemical purity of 99.42%.

Example 6

Preparation of the Crystal Form I of JK12A

Under nitrogen protection, 5 g of 5-methyltetrahydrofolate was dissolved in 40 g of water in a reaction flask with stirring, and then regulated with 10% sodium hydroxide solution to pH 7.5. After the solid was completely dissolved, 5 g of active carbon was added, and then sealed in an oxygen balloon overnight. After HPLC showed that the reaction of raw materials was completed, the system was filtered, and the filtrate was regulated with 50% acetic acid to pH 4.8 for crystallization. After filtration, the Filter cake was respectively washed with ethanol and acetone, and then 2.7 g of yellow solid JK12A was obtained through vacuum drying with chemical purity of 99.60%.

Example 7

Preparation of the Crystal Form I of JK12A

Under nitrogen protection, 5 g of 5-methyltetrahydrofolate was dissolved in 50 g of water in a reaction flask with stirring, and then regulated with 10% sodium hydroxide solution to pH 7.2. After the solid was completely dissolved, 4 g of active silica gel was added, and then sealed in an oxygen balloon overnight. After HPLC showed that the reaction of raw materials was completed, the system was filtered, and the filtrate was regulated with 50% acetic acid to pH 4.5 for crystallization. After filtration, the filter cake was respectively washed with ethanol and acetone, and then 2.3 g of yellow solid JK12A was obtained through vacuum drying with chemical purity of 98.41%.

Example 8

Preparation of the Crystal Form II of JK12A 2.0 g of JK12A was dissolved in 22 g of water in an ice water bath. 10% sodium hydroxide was added dropwise with stirring to regulate the solution to pH 6.7. After the solid was completely dissolved, the reaction solution was transferred to an ultrasonic device, and 50% acetic acid was added dropwise to regulate pH value of the solution to 5.2. 30 min later, the system was filtered, the filter cake was respectively washed with water, ethanol and acetone, and then 1.0 g of yellow solid JK12A was obtained through vacuum drying with chemical purity of 98.2%.

Example 9

Preparation of the Crystal Form II of JK12A 5.0 g of JK12A was dissolved in 50 g of water in an ice water bath. 10% sodium hydroxide was added dropwise with stirring to regulate the solution to pH 7.5. After the solid was completely dissolved, the reaction solution was transferred to an ultrasonic device, and 50% acetic acid was added dropwise to regulate pH value of the solution to 4.0. 30 min later, the system was filtered, the filter cake was respectively washed with water, ethanol and acetone, and then 2.2 g of yellow solid JK12A was obtained through vacuum drying with chemical purity of 98.5%.

Example 10

Preparation of the Crystal Form II of JK12A 8.0 g of JK12A was dissolved in 120 g of water in an ice water bath. 10% sodium hydroxide was added dropwise with stirring to regulate the solution to pH 8.0. After the solid was completely dissolved, the reaction solution was transferred to an ultrasonic device, and 50% acetic acid was added dropwise to regulate pH value of the solution to 5.0. 30 min later, the system was filtered, the filter cake was respectively washed with water, ethanol and acetone, and then 5.2 g of yellow solid JK12A was obtained through vacuum drying with chemical purity of 98.7%.

Example 11

Preparation of the Calcium Salt of JK12A 4.0 g of JK12A was dissolved in 20 g of water with stirring at room temperature. 10% sodium hydroxide was added to regulate the solution to pH 7.0. After the solid was completely dissolved, the reaction solution was cooled to 10° C. 4.0 g of 50% calcium chloride solution was added with stirring for 10 min. Then 25 mL of ethanol was added. After kept in an ultrasonic device for 30 min, the system was filtered, the filter cake was respectively washed with ethanol and acetone, and then 3.5 g of calcium salt of JK12A was obtained through vacuum drying with chemical purity of 97.6%.

Example 12

Reduction of JK12A 3.0 g of JK12A (purity 96.64%) was dissolved in 60 g of water, and then regulated with 10% sodium hydroxide to pH 7.0 with stirring. After the solid was completely dissolved, 2 g of KBH$_4$ was slowly added with further stirring for 1 hour. Results indicate that the content of 5-methyltetrahydrofolate was 71.26% in the reaction solution.

Example 13

Reduction of JK12A 3 g of JK12A (purity 96.64%) was dissolved in 60 g of water, and then regulated with 10% sodium hydroxide to pH 7.2 with stirring. After the solid was completely dissolved, 2 g of NaBH$_4$ was slowly added with further stirring for 1.5 hours. Results indicate that the content of 5-methyltetrahydrofolate was 79.32% in the reaction solution.

Example 14

Reduction of JK12A 10 g of JK12A (purity 96.64%) was dissolved in 150 g of water, and then regulated with 10% sodium hydroxide to pH 7.0 with stirring. After the solid was completely dissolved, 1.0 g of Pd/C was added, and fully stirred. After H$_2$ was insufflated, the system was pressurized to 0.2 MPa, and stirred for 2 h. Results indicate that the content of 5-methyltetrahydrofolate was 70.32% in the reaction solution.

Example 15

Purification of 5-methyltetrahydrofolate 10 g of 5-methyltetrahydrofolate (chemical purity 82%, optical purity 90%) was dissolved in 1000 g of water, and then regulated with 10% sodium hydroxide to pH 7.0 with stirring. After the solid was completely dissolved, 5 g of active carbon was added, and sealed in an oxygen balloon. After HPLC showed that the reaction of raw materials was completed, the system was filtered, and the filtrate was regulated with 10% hydrochloric acid to pH 3.0 for crystallization. After filtration, the filter cake was respectively washed with ethanol and acetone, and then 5.2 g of yellow solid JK12A was obtained through vacuum drying with chemical purity of 97.8%. The solid was added into 80 g of water, and then regulated with 10% sodium hydroxide to pH 7.0 with stirring. 12 g of sodium borohydride was slowly added. 4 hours later, the solution was regulated with 10% hydrochloric acid to pH 3.0 for crystallization. After filtration, the filter cake was respectively washed with ethanol and acetone, and then 2.9 g of 5-methyltetrahydrofolate was obtained through vacuum drying with chemical purity of 98.1% and optical purity of 96%.

Example 16

Immune Bioactivity

Experimental Method

Preparation of Murine Splenic Lymphocytes

After mice were killed through spine dislocation, their spleen was taken aseptically to prepare a single cell suspension. Redblood cells were removed from red blood cell lysis buffer, and the cell concentration was regulated.

Effect of the compound on the activity of murine splenic lymphocytes was detected with CCK-8 method:

Murine splenic lymphocyte suspension was inoculated in 96-well plates with $5\times10^5$/well.

Different concentrations of the compound were added. Corresponding solvent control and nutrient solution background control were also arranged. The total volume was 200 µL. The suspension was cultivated in an incubator with 5% CO$_2$ at 37° C. for 48 hours. 8-10 hours before the cultivation was completed, CCK-8 solution was added. On completion of the cultivation, the OD value was measured with an ELIASA at 450 nm (reference 650 nm).

Effect of the compound on the proliferation function of murine splenic lymphocytes was detected with $^3$H-TdR incorporation method:

Murine splenic lymphocyte suspension was inoculated in 96-well plates with $5\times10^5$/well.

ConA (final concentration: 5 µg/ml) and different concentrations of the compound were added. Corresponding control well without ConA and control well without drugs were also arranged. The suspension was cultivated in an incubator with 5% CO$_2$ at 37° C. for 48 hours. 8 hours before the cultivation was completed, 25 µl of $^3$H-TdR(10 µCi/ml) was added to each well. The suspension was further cultivated until the experiment was completed. Cells were collected with a cell collector onto a glass fiber membrane. After adding scintillation solution, the count of 3H-TdR incorporated into cellular DNA was obtained from a Beta counter (MicroBeta Trilux, PerkinElmer). The cell proliferation was expressed in terms of CPM.

TABLE 7

| | Measured conc. | Average OD | SD | Cell survival rate | | T lymphocyte ConA stimulation Average CPM | SD | Tcell proliferation Evaluation on comprehensive activity enhanced/inhibitedpercentage |
|---|---|---|---|---|---|---|---|---|
| Control | | 0.122 | 0.003 | | Cell control Stimulation control | 43977 | 8000 | |
| JK12A | 100.000 | 0.089 | 0.002 | 73% | | | | |
| | 40.000 | 0.109 | 0.006 | 89% | | 43537 | 4110 | −1% |
| | 16.0 | 0.113 | 0.007 | 92% | | 36061 | 241 | −18% |
| | 6.4 | 0.103 | 0.007 | 84% | | 30784 | 3903 | −30% |
| | 2.56 | 0.076 | 0.008 | 62% | | 25507 | 10004 | −42% |
| | 1.024 | 0.073 | 0.014 | 59% | | 17590 | 8005 | −60% |

TABLE 7-continued

| | | | | | | | |
|---|---|---|---|---|---|---|---|
| 0.41 | 0.052 | 0.015 | 75% | 14073 | 10299 | −68% | |
| 0.164 | | | | 40459 | 7501 | −8% | |

According to the preliminary screening results, the compound JK12A has significant effect on inhibiting murine T lymphocyte proliferation (at 1,024 and 0.41 uM).

Example 17

X-Ray Diffraction Pattern Conditions and Data of the Crystal Form I of JK12A

Instrument model: Bruker D8 advance XRD
Diffracted ray: CuKα radiation (40 kV, 40 mA)
Scan rate: 8°/min (2θ value)
Scan range: 5°~45° (2θ value)
Peak Search Report (41 Peaks, Max P/N=25.4)
PEAK: 27-pts/ParaBolic Filter, Threshold=3.0, Cut-off=0.1%, BG=3/1.0, Peak-Top=Summit

TABLE 8

X-ray diffraction pattern data of the crystal form I of JK12A

| # | 2θ | d(Å) | BG | Height | I % | Area | I % | FWHM |
|---|---|---|---|---|---|---|---|---|
| 1 | 7.759 | 11.3855 | 515 | 711 | 21.6 | 14304 | 12.2 | 0.342 |
| 2 | 12.001 | 7.3686 | 811 | 1923 | 58.4 | 36858 | 31.4 | 0.326 |
| 3 | 13.280 | 6.6614 | 882 | 1624 | 49.3 | 63703 | 54.3 | 0.667 |
| 4 | 13.641 | 6.4863 | 1170 | 2081 | 63.2 | 92889 | 79.1 | 0.759 |
| 5 | 14.040 | 6.3024 | 1509 | 1831 | 55.6 | 41910 | 35.7 | 0.389 |
| 6 | 15.121 | 5.8542 | 1296 | 1328 | 40.4 | 26130 | 22.3 | 0.334 |
| 7 | 15.821 | 5.5971 | 1162 | 1426 | 43.3 | 19410 | 16.5 | 0.231 |
| 8 | 16.939 | 5.2298 | 969 | 1637 | 49.7 | 32946 | 28.1 | 0.342 |
| 9 | 17.520 | 5.0578 | 1118 | 715 | 21.7 | 10094 | 8.6 | 0.240 |
| 10 | 19.119 | 4.6382 | 917 | 3291 | 100.0 | 117380 | 100.0 | 0.606 |
| 11 | 19.640 | 4.5163 | 821 | 2469 | 75.0 | 45052 | 38.4 | 0.310 |
| 12 | 20.293 | 4.3724 | 834 | 131 | 4.0 | 1110 | 0.9 | 0.144 |
| 13 | 21.180 | 4.1913 | 887 | 524 | 15.9 | 13519 | 11.5 | 0.439 |
| 14 | 22.023 | 4.0328 | 865 | 276 | 8.4 | 5088 | 4.3 | 0.313 |
| 15 | 22.941 | 3.8734 | 988 | 959 | 29.1 | 17399 | 14.8 | 0.308 |
| 16 | 24.020 | 3.7019 | 1361 | 1373 | 41.7 | 31757 | 27.1 | 0.393 |
| 17 | 24.440 | 3.6391 | 1188 | 2088 | 63.4 | 58657 | 50.0 | 0.478 |
| 18 | 25.042 | 3.5530 | 1445 | 444 | 13.5 | 7410 | 6.3 | 0.284 |
| 19 | 25.559 | 3.4822 | 1110 | 638 | 19.4 | 6104 | 5.2 | 0.163 |
| 20 | 26.718 | 3.3337 | 955 | 702 | 21.3 | 11858 | 10.1 | 0.287 |
| 21 | 27.581 | 3.2314 | 1010 | 1376 | 41.8 | 39313 | 33.5 | 0.486 |
| 22 | 28.039 | 3.1796 | 989 | 1111 | 33.8 | 39585 | 33.7 | 0.606 |
| 23 | 29.019 | 3.0745 | 941 | 833 | 25.3 | 11044 | 9.4 | 0.225 |
| 24 | 29.921 | 2.9838 | 828 | 1160 | 35.2 | 22209 | 18.9 | 0.325 |
| 25 | 30.919 | 2.8897 | 676 | 381 | 11.6 | 7114 | 6.1 | 0.317 |
| 26 | 32.319 | 2.7676 | 743 | 1000 | 30.4 | 31248 | 26.6 | 0.531 |
| 27 | 33.062 | 2.7072 | 876 | 153 | 4.6 | 888 | 0.8 | 0.099 |
| 28 | 33.499 | 2.6729 | 858 | 280 | 8.5 | 5549 | 4.7 | 0.337 |
| 29 | 33.880 | 2.6436 | 759 | 468 | 14.2 | 13836 | 11.8 | 0.503 |
| 30 | 34.338 | 2.6094 | 710 | 386 | 11.7 | 8649 | 7.4 | 0.381 |
| 31 | 35.818 | 2.5049 | 634 | 501 | 15.2 | 10222 | 8.7 | 0.347 |
| 32 | 36.700 | 2.4467 | 630 | 335 | 10.2 | 9973 | 8.5 | 0.506 |
| 33 | 37.980 | 2.3672 | 630 | 128 | 3.9 | 4291 | 3.7 | 0.570 |
| 34 | 38.296 | 2.3483 | 641 | 142 | 4.3 | 1751 | 1.5 | 0.210 |
| 35 | 38.941 | 2.3109 | 665 | 340 | 10.3 | 5087 | 4.3 | 0.254 |
| 36 | 39.476 | 2.2808 | 651 | 136 | 4.1 | 3806 | 3.2 | 0.476 |
| 37 | 40.444 | 2.2284 | 605 | 152 | 4.6 | 985 | 0.8 | 0.110 |
| 38 | 42.020 | 2.1484 | 445 | 216 | 6.6 | 8224 | 7.0 | 0.647 |
| 39 | 42.360 | 2.1320 | 452 | 169 | 5.1 | 6117 | 5.2 | 0.615 |
| 40 | 44.098 | 2.0519 | 494 | 166 | 5.0 | 4528 | 3.9 | 0.464 |
| 41 | 44.422 | 2.0377 | 537 | 172 | 5.2 | 3979 | 3.4 | 0.393 |

Example 18

X-Ray Diffraction Pattern Conditions and Data of the Crystal Form II of JK12A

Instrument model: Broker D8 advance XRD
Diffracted ray: CuKα radiation (40 kV, 40 mA)
Scan rate: 8°/min (2θ value)
Scan range: 5°~45° (2θ value)
Peak Search Report (45 Peaks, Max P/N=32.8)
PEAK: 21-pts/ParaBolic Filter, Threshold=3.0, Cut-off=0.1%, BG=3/1.0, Peak-Top=Summit

TABLE 9

X-ray diffraction pattern data of the crystal form II of JK12A

| # | 2θ | d(Å) | BG | Height | I % | Area | I % | FWHM |
|---|---|---|---|---|---|---|---|---|
| 1 | 6.802 | 12.9849 | 441 | 2177 | 43.6 | 38932 | 29.4 | 0.304 |
| 2 | 7.882 | 11.2075 | 458 | 98 | 2 | 548 | 0.4 | 0.095 |
| 3 | 9.054 | 9.7587 | 446 | 318 | 6.4 | 4551 | 3.4 | 0.243 |
| 4 | 12.159 | 7.2733 | 757 | 4722 | 94.5 | 91934 | 69.5 | 0.331 |
| 5 | 12.631 | 7.0024 | 906 | 511 | 10.2 | 3179 | 2.4 | 0.106 |
| 6 | 13.241 | 6.681 | 886 | 2183 | 43.7 | 75245 | 56.9 | 0.586 |
| 7 | 13.66 | 6.477 | 797 | 4995 | 100 | 132219 | 100 | 0.45 |
| 8 | 13.899 | 6.3661 | 798 | 2640 | 52.9 | 123894 | 93.7 | 0.798 |
| 9 | 14.903 | 5.9395 | 728 | 571 | 11.4 | 6392 | 4.8 | 0.19 |
| 10 | 15.938 | 5.556 | 700 | 3967 | 79.4 | 62015 | 46.9 | 0.266 |
| 11 | 16.761 | 5.285 | 659 | 827 | 16.6 | 14318 | 10.8 | 0.294 |
| 12 | 17.358 | 5.1047 | 664 | 1072 | 21.5 | 14176 | 10.7 | 0.225 |
| 13 | 18.36 | 4.8282 | 736 | 4076 | 81.6 | 64427 | 48.7 | 0.269 |
| 14 | 19.158 | 4.6289 | 485 | 2105 | 42.1 | 35665 | 27 | 0.288 |
| 15 | 19.581 | 4.5299 | 753 | 504 | 10.1 | 5465 | 4.1 | 0.184 |
| 16 | 21.079 | 4.2112 | 607 | 1678 | 33.6 | 32369 | 24.5 | 0.328 |
| 17 | 21.96 | 4.0441 | 620 | 1720 | 34.4 | 25073 | 19 | 0.248 |
| 18 | 23.019 | 3.8605 | 553 | 1857 | 37.2 | 25628 | 19.4 | 0.235 |
| 19 | 24.28 | 3.6627 | 763 | 765 | 15.3 | 14228 | 10.8 | 0.316 |
| 20 | 24.861 | 3.5785 | 916 | 1834 | 36.7 | 35340 | 26.7 | 0.328 |
| 21 | 26.001 | 3.4241 | 707 | 1953 | 39.1 | 29063 | 22 | 0.253 |
| 22 | 26.745 | 3.3305 | 635 | 1184 | 23.7 | 18539 | 14 | 0.266 |
| 23 | 27.721 | 3.2154 | 610 | 1411 | 28.2 | 30555 | 23.1 | 0.368 |
| 24 | 28.34 | 3.1466 | 578 | 866 | 17.3 | 14546 | 11 | 0.286 |
| 25 | 29.701 | 3.0054 | 664 | 468 | 9.4 | 6144 | 4.6 | 0.223 |
| 26 | 30.281 | 2.9491 | 666 | 2674 | 53.5 | 51357 | 38.8 | 0.327 |
| 27 | 31.836 | 2.8085 | 600 | 261 | 5.2 | 1807 | 1.4 | 0.118 |
| 28 | 32.239 | 2.7743 | 538 | 337 | 6.7 | 8170 | 6.2 | 0.412 |
| 29 | 32.643 | 2.7409 | 552 | 344 | 6.9 | 8454 | 6.4 | 0.418 |
| 30 | 32.918 | 2.7187 | 583 | 355 | 7.1 | 3694 | 2.8 | 0.177 |
| 31 | 33.52 | 2.6712 | 657 | 933 | 18.7 | 10292 | 7.8 | 0.188 |
| 32 | 34.12 | 2.6256 | 584 | 569 | 11.4 | 9227 | 7 | 0.276 |
| 33 | 34.72 | 2.5816 | 606 | 915 | 18.3 | 16472 | 12.5 | 0.306 |
| 34 | 35.684 | 2.514 | 493 | 472 | 9.4 | 7030 | 5.3 | 0.253 |
| 35 | 36.589 | 2.4539 | 495 | 213 | 4.3 | 2153 | 1.6 | 0.172 |
| 36 | 36.962 | 2.43 | 473 | 402 | 8 | 9635 | 7.3 | 0.407 |
| 37 | 37.523 | 2.3949 | 549 | 166 | 3.3 | 1503 | 1.1 | 0.154 |
| 38 | 39.041 | 2.3052 | 408 | 203 | 4.1 | 1347 | 1 | 0.113 |
| 39 | 39.557 | 2.2764 | 423 | 334 | 6.7 | 6005 | 4.5 | 0.306 |
| 40 | 40.596 | 2.2205 | 410 | 159 | 3.2 | 2271 | 1.7 | 0.243 |
| 41 | 41.123 | 2.1932 | 406 | 143 | 2.9 | 1150 | 0.9 | 0.137 |
| 42 | 41.668 | 2.1658 | 380 | 210 | 4.2 | 836 | 0.6 | 0.068 |
| 43 | 41.979 | 2.1504 | 387 | 335 | 6.7 | 2962 | 2.2 | 0.15 |
| 44 | 43.119 | 2.0962 | 376 | 152 | 3 | 627 | 0.5 | 0.07 |
| 45 | 44.092 | 2.0521 | 371 | 129 | 2.6 | 938 | 0.7 | 0.124 |

The invention claimed is:
1. A compound having a structural formula of formula I:

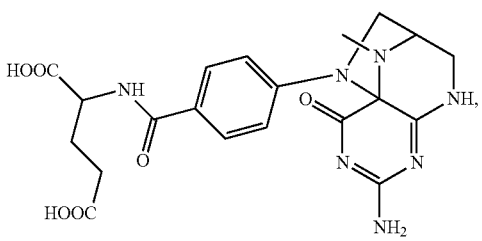

or a pharmaceutically acceptably salt thereof, or a stereoisomer of the compound of formula I.

2. A salt of the compound of claim 1, wherein the salt is:
a pharmaceutically acceptable salt of the compound having the structural formula of formula I, or
a pharmaceutically acceptable salt of the stereoisomer of the compound having the structural formula of formula I.

3. The salt according to claim 2, wherein the salt is a calcium salt.

4. A crystal of the compound of claim 1, where the crystal has a crystal form I or II, wherein:
the crystal form I exhibits diffraction peaks in a X-ray diffraction pattern at 2θ angle of 13.3±0.2, 14.0±0.2, 16.9±0.2, 19.1±0.2, 24.4±0.2 and 27.6±0.2; and
the crystal form II exhibits diffraction peaks in a X-ray diffraction pattern at 2θ angle of 6.8±0.2, 12.2±0.2, 13.7±0.2, 15.9±0.2, 18.4±0.2 and 23.0±0.2.

5. The crystal of the compound of claim 4, wherein:
the diffraction peaks are present in the X-ray diffraction pattern of the crystal form I at 2θ angle of 13.3, 14.0, 16.9, 19.1, 24.4 and 27.6; and
the diffraction peaks are present in the X-ray diffraction pattern of the crystal form II at 2θ angle of 6.8, 12.2, 13.7, 15.9, 18.4 and 23.0.

6. A method of preparing the crystal of claim 4, where the crystal is of the crystal form I, the method comprising the following steps:
a) adding the 5-methyltetrahydrofolate into a polar medium to form a first solution;
b) regulating the pH of the first solution with alkali to form a second solution with a pH in a range of from 6 to 8;
c) adding to the second solution an oxidizing agent with stirring to form a third solution;
d) regulating the pH of the third solution with acid to form a fourth solution with a pH in a range of from 3 to 5; and
e) crystallizing the crystal form I of the compound of formula I from the fourth solution.

7. The method according to claim 6, wherein, in the step a), the polar medium is water or a mixture of water and a water-miscible organic solvent.

8. The method according to claim 6, wherein, in the step b), the alkali is organic alkali or inorganic alkali.

9. The method according to claim 6, wherein, in the step c), the oxidizing agent is air, or oxygen or hydrogen peroxide.

10. The method according to claim 8, wherein, the inorganic alkali is selected from the group consisting of potassium hydroxide, sodium hydroxide, calcium hydroxide, magnesium hydroxide, potassium carbonate, sodium carbonate, potassium bicarbonate, and sodium bicarbonate; and the organic alkali is selected from the group consisting of ammonia, monomethylamine, 4-dimethylpyridine and piperazine.

11. The method according to claim 6, wherein, in the step d), the acid is organic acid or inorganic acid.

12. The method according to claim 11, wherein, the inorganic acid is selected from the group consisting of hydrochloric acid, sulfuric acid and hydrobromic acid; and the organic acid is selected from the group consisting of formic acid, acetic acid and phenylmethanesulfonic acid.

13. The method according to claim 6, further comprising a step of adding high active surfactant before the step c), wherein, the high active surfactant is selected from the group consisting of active carbon, active silica gel and active aluminum oxide, where an amount of the high active surfactant is in a range of from 0.05 to 10 times the mass of the 5-methyltetrahydrofolate added in the step a).

14. A method of preparing the crystal of claim 4, where the crystal is of crystal form II, the method comprising:
crystallization of the compound of formula I with the aid of ultrasonication in a polar medium at pH≥3.

15. The method according to claim 14, wherein, the polar medium is water or a mixture of water and a polar water-soluble organic solvent.

16. A method of preparing the crystal of claim 4, where the crystal is of crystal form II, the method comprising the following steps:
a) adding a solid form of the compound of formula I into a polar medium to form a first solution comprising a solid;
b) regulating the pH of the first solution with alkali to form a second solution with a pH in a range of from 6 to 10, wherein the pH is regulated until the solid is dissolved; and
c) crystallizing the compound of formula I with the aid of ultrasonication, then regulating the pH of the second solution with acid to form a third solution with a pH in a range of from 3 to 6.

17. The method according to claim 16, wherein, in the step b), the alkali is organic alkali or inorganic alkali.

18. The method according to claim 17, wherein, the inorganic alkali is selected from the group consisting of potassium hydroxide, sodium hydroxide, calcium hydroxide, magnesium hydroxide, potassium carbonate, sodium carbonate, potassium bicarbonate, and sodium bicarbonate; and the organic alkali is selected from the group consisting of ammonia, monomethylamine, 4-dimethylpyridine and piperazine.

19. The method according to claim 16, wherein, in the step c), the acid is organic acid or inorganic acid.

20. The method according to claim 19, wherein, the inorganic acid is selected from the group consisting of hydrochloric acid, sulfuric acid and hydrobromic acid; and the organic acid is selected from the group consisting of formic acid, acetic acid and phenylmethanesulfonic acid.

21. A method of preparing a compound of formula II:

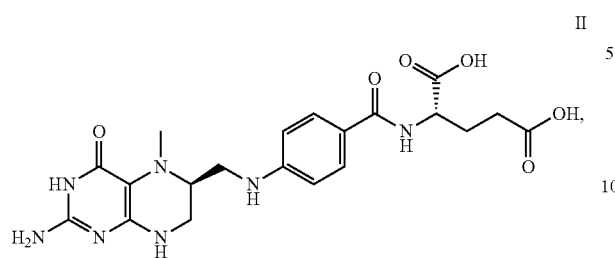

the method comprising:
reducing the compound of formula I according to claim 1

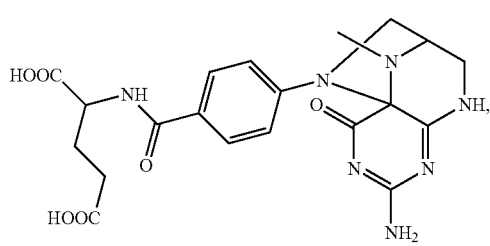

to obtain the compound of formula II.

22. The method according to claim 21, wherein, reducing the compound of formula I to obtain the compound of formula II comprises:

dissolving the compound of formula I in water in the presence of alkali, and then reacting the compound of formula I with a reducing agent; and obtaining the compound of formula II through separation.

23. The method according to claim 22, wherein, the reducing agent is borohydride, or reducing gas, or sulfhydryl compound.

24. The method according to claim 23, wherein, the borohydride is selected from the group consisting of sodium borohydride, potassium borohydride, and potassium tri-tert-butyl-borohydride; the reducing gas is selected from the group consisting of $H_2$ and borane; and the sulfhydryl compound is selected the group consisting of from mercaptoethanol, cysteine and mesna.

25. A pharmaceutical composition comprising a compound of claim 1 and a pharmaceutically acceptable carrier.

26. The method according to claim 13, wherein the amount of the high active surfactant is in a range of from 0.5 to 2 times the mass of the 5-methyltetrahydrofolate added in the step a).

* * * * *